United States Patent [19]

Hinchliffe et al.

[11] Patent Number: 5,637,504
[45] Date of Patent: Jun. 10, 1997

[54] STABLE YEAST 2 μM VECTOR

[75] Inventors: Edward Hinchliffe, Burton Joyce; Simon A. Chinery, Bingham, both of United Kingdom

[73] Assignee: Delta Biotechnology Limited, Nottingham, United Kingdom

[21] Appl. No.: 308,479

[22] Filed: Sep. 19, 1994

Related U.S. Application Data

[63] Continuation of Ser. No. 908,496, Jun. 30, 1992, abandoned, and Ser. No. 177,139, Apr. 4, 1988, abandoned.

[30] Foreign Application Priority Data

Apr. 9, 1987 [GB] United Kingdom ............... 8708495
Aug. 3, 1987 [GB] United Kingdom ............... 8718347

[51] Int. Cl.$^6$ ............... C12N 15/00; C12N 1/16; C12P 21/06; C12P 1/02
[52] U.S. Cl. ............... 435/320.1; 435/69.1; 435/69.2; 435/71.1; 435/171; 435/172.1; 435/172.3; 435/255.1; 935/6; 935/9; 935/22; 935/33; 935/57; 935/59; 935/60; 935/61; 935/66; 935/69
[58] Field of Search ............... 435/69.1, 69.2, 435/71.1, 171, 172.1, 172.3, 256, 255.1, 320.1; 536/27; 935/6, 9, 22, 33, 57, 59, 60, 61, 66, 69

[56] References Cited

U.S. PATENT DOCUMENTS

| | | | |
|---|---|---|---|
| 4,588,684 | 5/1986 | Brake | 435/68 |
| 5,114,922 | 5/1992 | Maschler et al. | 514/12 |

FOREIGN PATENT DOCUMENTS

| | | | |
|---|---|---|---|
| 147198 | 7/1985 | European Pat. Off. | C12N 15/00 |
| 201239 | 11/1986 | European Pat. Off. | C12N 15/00 |
| 251744 | 1/1988 | European Pat. Off. | C12N 15/00 |
| 8703006 | 5/1987 | WIPO | C12P 7/06 |

OTHER PUBLICATIONS

Moniatis et al., 1982, Molocular Cloning, Cold Spring Harbor Laboratory pp. 11–15.
Meader et al., 1985, Gene, 34:325–334.
Andrews et al., 1985, Cell, vol. 40:795–803.
Hartley & Donelson (1980) Nature, 286, pp. 860–865.
Knowlton, "Copy Number and Stability of Yeast Plasmids", in Maximising Gene Expression, Eds. Reznikoff 7 Gold, Butterworths, 1986.
Jayaram et al (1983) Cell 34, pp. 95–104.
Volkert & Broach (1986) Cell 45, pp. 541–550.
Futcher (1988) Yeast, vol. 4, 27–40.
Broach (1983) Methods In Enzymology, vol. 101, 307–325.
Hinchcliffe et al (1985), Proc. Brew. Conf. Cong. 20th (Helsinki) 267–274.
Gerbaud et al (1979) Gene 5, 233,253.
Broach & Hicks (1980) Cell 21, 501–508.
Vetter et al (1983) P.N.A.S. 80, 7284–7288.
Bruschi (1986) 13th Int. Conf. on Yeast Genetics and Mol. Biol., 544.
Feng et al (1986) Proc. Natl. Sci. Counc. B. ROC 10, 175–183.
Sadowski, P. (1986) J. Bacter. 165, 341–347.
Reynolds et al (1987) Molecular and Cellular Biology 7, 3566–3573.
Toh–e et al (1980) J. Bact. 141(1), 413–416.
Struhl et al (1979) PNAS (76(3), 1035–1039.
Hollenberg et al, "Cloning with 2–μm DNA Vectors and the expression . . . " Microbiology B Immunology, vol. 96, 1982, pp. 119–144.
Biological Abstracts/RRM, "A New System for in–vivo Study of the Yeast", Bruschi et al.
Bachmair et al, "Construction of a Yeast Cloning Vector . . . " Monatshefte fur Chemie 115, 1229–1235 (1984).

Primary Examiner—Mindy Fleisher
Assistant Examiner—Bonnie D. Weiss
Attorney, Agent, or Firm—Steven J. Moore

[57] ABSTRACT

A 2 μm plasmid vector for transforming yeast, especially brewing yeast, much which comprises a DNA sequence allowing propagation of the plasmid in bacteria, two copies of the 74 base pair FLP recombination site of the 2 μm plasmid in direct orientation and a DNA sequence coding for a protein or peptide of interest. The plasmid is so constructed that in yeast the bacterial DNA sequence is between the two recombination sites which are in direct orientation and is spontaneously lost following recombination. A "gene of interest" is preferable inserted at the SnaBI site.

17 Claims, 6 Drawing Sheets

Fig. 5 pSAC3U2 pSAC300

Fig. 9  Co-Inheritance of URA+ and bla+

S150-2B cir+ (pSAC3U2)    cir° (pSAC3U2)

S150-2B cir+ (pSAC3U1)    cir° (pSAC3U1)

Fig. 10

STABLE YEAST 2 μM VECTOR

This is a continuation of application Ser. No. 07/908,496 filed Jun. 30, 1992 and application Ser. No. 07/177,139 filed Apr. 4, 1988, both abandoned.

BACKGROUND OF THE INVENTION

This invention relates to genetic engineering in yeast, especially Saccharomyces cerevisiae.

The uptake of exogenous DNA by yeast cells and the subsequent inheritance and expression of that DNA are brought about by a process called transformation. Transformation was first described in the late 1970's, employing methods which rely upon the addition of DNA to protoplasts produced by the enzymatic removal of the yeast cell wall (Hinnen et al., 1978; Beggs, 1978). More recently the transformation of intact yeast cells has been demonstrated (Hisao et al., 1983).

Yeast can be transformed by appropriate plasmids; plasmids used for this purpose are usually constructed as "shuttle vectors" which can be propagated in either *Escherichia coli* or yeast (Hinnen et al., 1978; Beggs, 1978; Struhl, et al., 1979). The inclusion of *E. coli* plasmid DNA sequences, such as pBR322 (Bolivar, 1978), facilitates the quantitative preparation of vector DNA in *E. coli*, and thus the efficient transformation of yeast.

Plasmid vectors commonly in use for yeast transformation can be divided into two types: (i) replicating vectors, that is those which are capable of mediating their own maintenance, independent of the chromosomal DNA of yeast, by virtue of the presence of a functional origin of DNA replication and (ii) integrating vectors, which rely upon recombination with the chromosomal DNA to Facilitate replication and thus the continued maintenance of the recombinant DNA in the host cell. Replicating vectors can be Further sub-divided into: (a) 2 μm-based plasmid vectors in which the origin of DNA replication is derived from the endogenous 2 μm plasmid of yeast, (b) autonomously replicating vectors (ARS) in which the "apparent" origin of replication is derived from the chromosomal DNA of yeast and (c) centromeric plasmids (CEN) which carry in addition to one of the above origins of DNA replication a sequence of yeast chromosomal DNA known to harbour a centromere.

In order to transform yeast efficiently with any of the aforementioned vectors it is necessary to impose a selection to identify those transformants which carry the recombinant DNA. This is achieved by incorporating within the vector DNA a gene with a discernible phenotype. In the case of vectors used to transform laboratory yeast, prototrophic genes, such as LEU2, URA3 or TRP1 (Hinnen et al., 1978; Beggs, 1978; Gerbaud et al, 1979), are usually used to complement auxotrophic lesions in the host. However, in order to transform brewing yeast and other industrial yeasts, which are frequently polyploid and do not display auxotrophic requirements, it is necessary to utilize a selection system based upon a dominant selectable gene. In this respect replicating 2 μm based plasmid vectors have been described carrying genes which mediate resistance to: (i) antibiotics, for example G418 (Jiminez et al., 1980; Webster et al., 1983), hygromycin B (Gritz et al., 1983), chloramphenicol (Cohen et al., 1980; Hadfield et al, 1986), and (ii) otherwise toxic materials, for example the herbicide sulfometuron methyl (Falco et al., 1985), compactin (Rine et al 1983) and copper (Henderson et al., 1985).

The inheritable stability of recombinant genes in yeast is dependent upon the type of yeast vector employed to facilitate transformation. The most stable of the two types of vector systems described earlier are the integrating vectors. The principles and practice of integrative yeast transformation have been described in the literature (Borsrein & Davis, 1982; Winston et al., 1983; Orr-Weaver et al., 1983; Rothstein, 1983). In general, integratire transformation is relatively inefficient; closed circular integrating plasmids have been described which yield approximately 1–10 transformants per ug of DNA (Hinnen et al., 1979; Hicks et al., 1979). However, linear DNA, with free ends located in DNA sequences homologous with yeast chromosomal DNA, transforms yeast with higher efficiency (100–1000 fold) and the transforming DNA is generally found integrated in sequences homologous to the site of cleavage (Orr-Weaver et al., 1981). Thus by cleaving the vector DNA with a suitable restriction endonuclease, it is possible to increase the efficiency of transformation and target the site of chromosomal integration. Integratire transformation is applicable to the genetic modification of brewing yeast, providing that the efficiency of transformation is sufficiently high and the target DNA sequence for integration is within a region that does not disrupt genes essential to the metabolism of the host cell. An integrating yeast vector has recently been described for brewing yeast (Yocum, 1985).

Unlike integrating vectors, which show a high degree of inheritable stability in the absence of selection, replicating vectors tend to be more unstable. The degree of inheritable stability is dependent upon the type of replicating vector used. ARS plasmids, which have a high copy number (approximately 20–50 copies per cell) (Hyman et al., 1982), tend to be the most unstable, and are lost at a frequency greater than 10% per generation (Kikuchi, 1983). However, the stability of ARS plasmids can be enhanced by the attachment of a centromere; centromeric plasmids are present at 1 or 2 copies per cell (Clarke & Carbon, 1980) and are lost at only approximately 1% per generation (Walmsley et al., 1983). Chimeeric 2 μm based plasmids show varying degrees of inheritable stability, dependent upon both the host strain and the 2 μm DNA sequences present on the plasmid.

The 2 μm plasmid is known to be nuclear in cellular location (Nelson & Fangman, 1979; Livingston & Hahne, 1979; Seligy et al., 1980; Taketo et al., 1980; Sigurdson et al., 1981), but is inherited in a non-Mendelian fashion (Livingston, 1977). Cells without the 2 μm plasmid (cir°) have been shown to arise from haploid yeast populations having an average copy number of 50 copies of the 2 μm plasmid per cell at a rate of between 0.001% and 0.01% of the cells per generation (Futcher & Cox, 1983). A possible explanation for this low level of inheritable instability is that the plasmid provides no obvious advantage to the cell under normal growth conditions (Broach, 1981; Futcher & Cox, 1983; Sigurdson et al., 1981), although small effects on growth rates have been reported for some strains harbouring the 2 μm plasmid (Walmsley et al., 1983). Analysis of different strains of *S. cerevisiae* has shown that the plasmid is present in most strains of yeast (Clark-Walker & Miklos, 1974) including brewing yeast (Tubb, 1980; Aigle et al., 1984; Hinchliffe & Daubhey, 1986). It thus appears that the plasmid is ubiquitous, which implies a high degree of inheritable stability in nature.

Genetic and molecular analysis of the 2 μm plasmid has revealed a wealth of information concerning the replication and stable maintenance of the plasmid (Volkert & Broach, 1987). In essence the plasmid consists of a circular DNA molecule of 6318 base-pairs (Hartley & Donelson, 1980). It harbours a unique bidirectional origin of DNA replication (Newlon et al., 1981) which is an essential component of all 2 μm based vectors. The plasmid contains Four genes, REP1, REP2, REP3 and FLP which are required for the stable maintenance of high plasmid copy number per cell (Broach & Hicks, 1980; Jaysram et al., 1983). The REP1 and REP2 genes encode trans acting proteins which are believed to function in concert by interacting with the REP3 locus to ensure the stable partitioning of the plasmid at cell division (Volkerr & Broach, 1987). In this respect, the REP3 gene behaves as a cis acting locus which effects the stable segregation of the plasmid, and is phenotypically analogous to a chromosomal centromere (Jaysram et al., 1983; Kikuchi, 1983). An important feature of the 2 μm plasmid is the presence of two inverted DNA sequence repetitions (each 559 base-pairs in length) which separate the circular molecule into two unique regions. Intramolecular recombination between the inverted repeat sequences results in the inversion of one unique region relative to the other and the production in vivo of a mixed population of two structural isomers of the plasmid, designated A and B (Beggs, 1978). Recombination between the two inverted repeats is mediated by the protein product of a gene called the FLP gene, and the FLP protein is capable of mediating high frequency recombination within the inverted repeat region. This site specific recombination event is believed to provide a mechanism which ensures the amplification of plasmid copy number (Futcher, 1986; Volkert & Broach, 1986; Som et al., 1988; Murray et al., 1987).

Each inverted repeat sequence comprises three DNA repeat sequences sub-units (depicted as triangles in FIG. 3), two adjacent sub-units being in mutually direct orientation and the third being in indirect orientation and joined to one of the other sub-units via an 8 base pair linking or spacer region. This spacer region contains a unique XbaI site and recognises and is cut at its margins by the product of the FLP gene. The adjacent sequences are of course homologous to the corresponding sequences of the other inverted repeat sequence and hence provide for accurate recombination following the said cutting. Andrews et al., (1985) has found that a 74 base pair sequence including the 8 b.p. spacer region is the minimum requirement for FLP site specific recombination.

Yeast vectors based upon the replication system of the 2 μm plasmid have been constructed by inserting heterologous DNA sequences in regions of the 2 μm plamid not essential to its replication (Beggs, 1981). This has resulted in two basic types of vector: (i) whole 2 μm vectors and (ii) 2 μm origin vectors. In the case of the former, these vectors harbour the whole 2 μm plasmid into which various heterologous sequences have been inserted, such as E. coli plasmid DNA. These plasmids are capable of maintaining themselves at high copy number with a high degree of inheritable stability in both cir$^+$ (2 μm containing) and cir$^°$ (2 μm deficient) hosts. On the other hand 2 μm origin vectors usually contain a minimal DNA sequence harbouring the 2 μm origin of DNA replication and a single copy of the 599 base-pair repeat of 2 μm; such vectors can only be maintained in cir$^{3o}$ host strains, since they require the proteins encoded by the REP1 and REP2 genes to be supplied in trans from the endogenous plasmid to ensure their 'stable' maintenance. When a genetically modified yeast which is capable of expressing a heterologous gene to produce high levels of a commercially important polypeptide is constructed, it is usually desirable to choose a high copy number yeast vector. 2 μm based vectors have proved very successful for use as expression plasmids and therefore frequently constitute the vector of choice (Kingsman et al., 1985).

In European Patent Application 86303039.1 (Publication No. 0201239 A1 in the name of Delta Biotechnology Ltd.) a process is described for the production of heterologous proteins in brewing yeast, in which an industrial yeast strain is genetically modified to be capable of expressing a heterologous gene, such that no expression of the said heterologous gene takes place during the primary beer fermentation, but rather yeast biomass is accumulated and the synthesis of heterologous protein is induced after the yeast has been removed from the beer. This is achieved by transforming brewing yeast with a 2 μm based plasmid harbouring the dominant selectable marker CUP-1 and a gene encoding a modified human serum protein, N-methionyl albumin (Met-HSA); whose expression is regulated at the transcriptional level by a galactose inducible promoter. In order to maximise the yield of heterologous protein synthesis during the operation of the said process it is necessary to ensure: (i) a high copy number of the gene to be expressed (encoding for Met-HSA); (ii) a high degree of inheritable stability of the gene of interest under conditions of non-selective growth; (iii) that the recombinant genes transformed into brewing yeast must not have a deleterious effect upon the yeast and its ability to produce beer and subsequently heterologous protein; and (iv) that the recombinant genes present in yeast should, so far as possible, be restricted to the 'gene of interest' and adjacent yeast regulatory genes. The requirement (ii) is particularly important because it is both impractical and undesirable to supplement the normal growth medium of brewers' yeast, namely hopped malt extract, with toxic materials such as copper ions since this will increase process costs and have a deleterious and probably unacceptable effect upon the quality of the beer, which is the primary product of the fermentation. In connection with requirement (iv), it is desirable that the genetically modified yeast should not possess extraneous DNA sequences such as those which are derived from the bacterial portion of the recombinant plasmid.

In our application published as EP-A-251744 we have described a method for modifying yeast cells by incorporating into the endogenous 2 μm plasmid a DNA sequence coding for a protein or peptide of interest, by making an integration vector comprising two copies of a homologous 2 μm plasmid DNA sequence in direct orientation encompassing the DNA sequence of interest, transforming yeast with the said integration vector, and then isolating from the transformed yeast obtained cells containing the endogenous 2 μm plasmid modified by incorporation of the DNA sequence of interest. The integration vector itself does not survive in the transformed yeast cells. The homologous 2 μm plasmid DNA sequences may be, but usually are not, copies of the plasmid repeat sequence.

BRIEF SUMMARY OF THE INVENTION

We have now found that a modification of the method of the said application make it possible to transform yeast cells by incorporation of a modified 2 μm plasmid.

In the method of the present application, the plasmid vector used comprises a DNA sequence which allows propagation of the vector in bacteria encompassed between two homologous 2 μm plasmid DNA FLP recombination sites in direct orientation, a DNA sequence coding for a protein or peptide of interest, which is preferably but not necessarily a sequence heterologous to yeast, and preferably also a selectable marker DNA sequence. The plasmid vector of the invention thus comprises three copies of the FLP recombination site of which one pair is in direct orientation and the other two pairs are in indirect orientation. When yeast is transformed with a plasmid vector having this construction, the DNA sequence which allows propagation of the vector in bacteria has been found to be spontaneously lost and the plasmid vector becomes a modified 2 μm plasmid which is capable of replacing the endogenous 2 μm plasmid in the transformed yeast. Plasmid vectors of this type are hereinafter called disintegration vectors. The yeast transformed with such vectors may contain multiple extrachromosomal copies of a modified 2 μm plasmid containing a gene of interest but no bacterial DNA, which have been found to be stably inherited under conditions of non-selective growth.

Bruschi (13th International Conference on Yeast Genetics and Molecular Biology, Autumn 1986) disclosed that recombination in a 2 μ-based plasmid could result in the excision of bacterial DNA sequences, but suggested only that the system could be used to study structure-function relationships in the DNA molecule. We have now found that a similar system can be used to prepare advantageous expression vectors which have unexpected stability.

The term "FLP recombination site" is used herein to mean any site which will allow for recombination as a result of interaction with the FLP Eene product. If Andrews' finding (1985) is correct, then the FLP recombination site will generally comprise as a minimum the 74 b.p. sequence identified by him. In practice, there is no point in including more than the 599 base pairs of the whole repeat sequence.

The 2 μm based disintegration vector of the present invention has been found to be capable of transforming both laboratory and industrial yeast. The disintegration vector is maintained at a high copy number per cell and has an extremely high degree of inheritable stability. In addition, unlike all other 2 μm based plasmid vectors thus far described, the disintegration vector is constructed so that, upon transformation of yeast, the bacterial plasmid DNA sequences are spontaneously deleted. Thus genetically modified strains of brewing Feast can be constructed in which the 'gene of interest' incorporated in the 2 μm plasmid is stably maintained, even under conditions of non-selective growth, at a high copy number per cell, in the absence of extraneous bacterial plasmid DNA sequences. The use of such a vector in the construction of a genetically modified brewing yeast ensures that only the 'gene of interest' is stably maintained fop successive generations in brewing yeast, thereby circumventing any potential deleterious effects that additional DNA sequences may have upon the technological behaviour of the yeast and/or the flavour and quality characteristics of beer produced by the yeast.

In practice the 'gene of interest' can be any recombinant gene, either homologous or heterologous to yeast. The distintegration vector can be used for example to stably integrate the Met-HSA gene in brewing yeast expressed from either a constitutive yeast promoter, for example the phosphoglycerate kinase promoter (PGK) in accordance with the method described in EP-A-147 198 or a regulated yeast promoter, for example the GAL10/CYC1 hybrid promoter as described in EP-A-201 239, or the GAL/PGK promoter as described in EP-A-258 067.

Additional genes which may be stably maintained by this system include the DEX1 gene of *Saccharomyces diastaticus* which specifies the production of an extra-cellular glucoamylase enzyme in brewing yeast, and the β-glucanase gene of *Bacillus subtilis* which specifies the production of an endo-1,2-1,4-β-glucanase in brewing yeast (Hinchliffe & Box, 1985). Such genes can be first genetically modified to control the level of gene expression and/or to ensure that the protein whose synthesis is mediated by the gene is secreted by the brewing yeast.

The use of the new disintegration vector is particularly advantageous in the process described in EP-A-201 239, since, according to this process, the 'gene of interest' is regulated so that it is not expressed during the course of the beer fermentation nor under normal conditions of yeast growth, but is rather induced in a post fermentation process. Consequently high level expression of the 'gene of interest' is divorced in time from the synthesis of yeast biomass by cell proliferation, and thus any adverse effects of gene expression upon plasmid stability are minimized.

Preferably the vector of the present invention is a disintegration vector (as hereinbefore defined) comprising a complete 2 μm plasmid additionally carrying (i) a bacterial plasmid DNA sequence necessary for propagation of the vector in a bacterial host; (ii) an extra 2 μm FLP recombination site; (iii) a DNA sequence coding for a desired protein or peptide; and (iv) a selectable marker DNA sequence for yeast transformation; the said bacterial plasmid DNA sequence being present and the extra FLP recombination site being created at a restriction site in one of the two inverted repeat sequences of the 2 μm plasmid; the said extra FLP recombination site being in direct orientation in relation to the endogenous FLP recombination site of the said one repeat sequence, and the bacterial plasmid DNA sequence being sandwiched between the extra FLP recombination site and the endogenous FLP recombination site of the said one repeat sequence.

Figure 3:
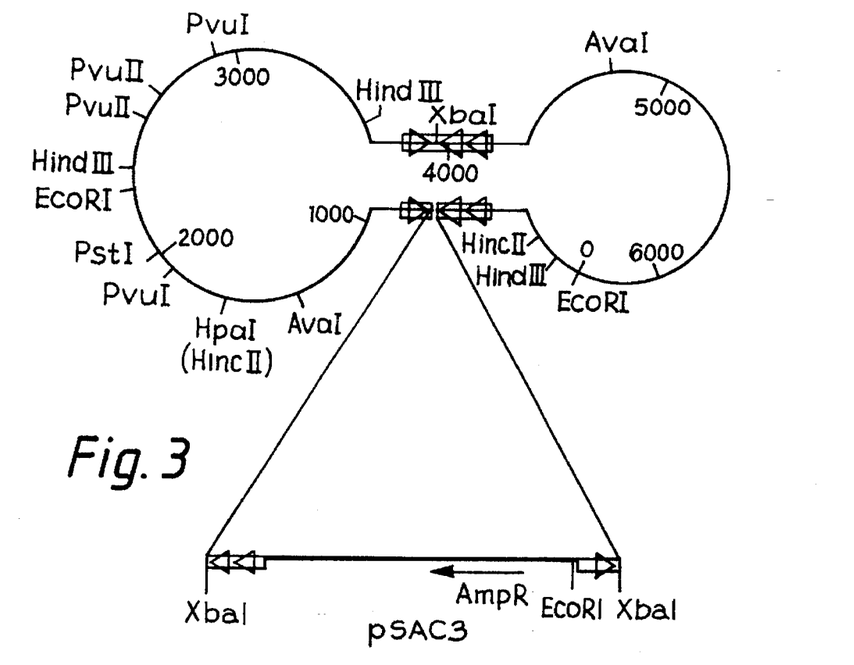
FIG. 3 shows plasmid pSAC3. The thick line represents DNA sequences from the bacterial plasmid pUC9; the open bars represent the 74 base-pair DNA fragment containing the FLP recombination site; the thin line represents 2 μm plasmid DNA sequences; the triangles indicate the orientation of the three internal DNA repeats in each FLP recombination site.

The preferred disintegration vector thus consists of a complete 2 μm plasmid into which is inserted one or more bacterial plasmid DNA sequences and an extra copy of a 74 base-pair FLP recombination site derived from the 2 μm plasmid. In addition the 'gene of interest', co-linear with a selectable marker for yeast transformation, e.g. CUP-1, is inserted at a second site in the 2 μm plasmid. The bacterial plasmid DNA sequences and yeast DNA repeat are inserted, e.g. at an XbaI site, in one copy of the two inverted repeats of the whole 2 μm plasmid. The correct orientation of the DNA repeat is essential to the function of the plasmid; the plasmid is constructed so that the bacterial plasmid sequence necessary for DNA propagation in, for example, *E. coli*, is sandwiched between two copies of the FLP recombination site of the 2 μm plasmid, which are themselves in direct orientation. The configuration of DNA sequences is illustrated in FIG. 3 described in more detail below. This construction confines the bacterial plasmid DNA sequences to a region of DNA which, when the plasmid is transformed into yeast, is excised from the plasmid, by virtue of a site-specific recombination event between the two directly oriented DNA repeats. This site-specific recombination is mediated by the product of the FLP gene of 2 μm whose product can either be supplied by the endogenous 2 μm plasmid of yeast, when transforming cir$^+$ cells, or by the disintegration vector itself when transforming cir° cells. Because the vectors of the invention may be used to cure the transformed yeast of its endogenous 2 μm plasmids, and also because the recombination is more rapid in cir° cells, it is preferable for the vector of the invention to be based on a complete 2 μm plasmid. If however, the vector of the invention is to co-exist with the endogenous 2 μm plasmids, then genes such as REP1, REP2, REP3 and FLP need not be present on the vector, as the products of these genes can be supplied in trans; all that is necessary is an origin of replication.

As is described in more detail below, the inserted DNA carrying the bacterial sequences may carry at each end a respective portion of the repeat sequence, in which case the said DNA is inserted into an endogenous repeat sequence such that the endogenous recombination site is effectively destroyed but two new FLP recombination sites are formed, each comprising a portion of the endogenous recombination site and a complementary portion from the inserted DNA. Alternatively, a complete FLP recombination site may be carried towards one end of the insert, which insert is then inserted adjacent to or spaced from an endogenous repeat sequence such that the bacterial DNA lies between the endogenous repeat sequence and the inserted repeat sequence. When the inserted DNA is inserted at a location spaced from the endogenous sequence, the endogenous DNA between the endogenous repeat sequence and the inserted repeat sequence will later be excised along with the bacterial DNA. Hence, if this DNA is needed, a further copy of it must be provided (preferably on the inserted DNA) on the side of the inserted repeat sequence remote from the endogenous repeat sequence.

The site within the integral 2 μm plasmid at which the 'gene of interest' is inserted is chosen with a view to minimizing the effect of the insertion upon both plasmid copy number and inheritable stability. Thus it is advantageous to insert the 'gene of interest' at a site that does not interrupt the integrity of the REP1, REP2, REP3 and FLP genes, particularly if the plasmid is intended for use in the transformation of a cir° host strain of yeast.

One advantageous characteristic of the disintegration vector is that, when it is introduced into cir⁺yeast strains, because it possesses an integral 2 μm plasmid, it is capable of curing the endogenous plasmid, either during or following the excision of the bacterial plasmid sequences. An analogous situation has recently been reported for whole 2 μm vectors transformed into cir⁺host strains of yeast (Hatford & Peters, 1987). Thus the disintegration vector can also be used to cure the endogenous 2 μm plasmid from strains of yeast.

It is to be noted that plasmids may also be created which, before recombination, have only two FLP recombination sites, in direct orientation and with the unwanted, for example bacterial, DNA between them (i.e. as the shorter of the two parts of the plasmid separated by the pair of recombination sites). After recombination, the plasmid will have only one recombination site and will therefore not undergo the usual 2 μm recombination to give a mixed population of A and B forms. Such plasmids are likely to be less stable than those described above, but nevertheless form an aspect of the invention and may be claimed as such.

BRIEF DESCRIPTION OF THE DRAWINGS

In the accompanying drawings,

FIG. 8 is a plasmid map of pSAC310. Designations are as for FIG. 3;

The following Examples illustrate the invention.

DETAILED DESCRIPTION OF PREFERRED EMBODIMENTS

EXAMPLE I

Construction of Plasmids

Figure 1:
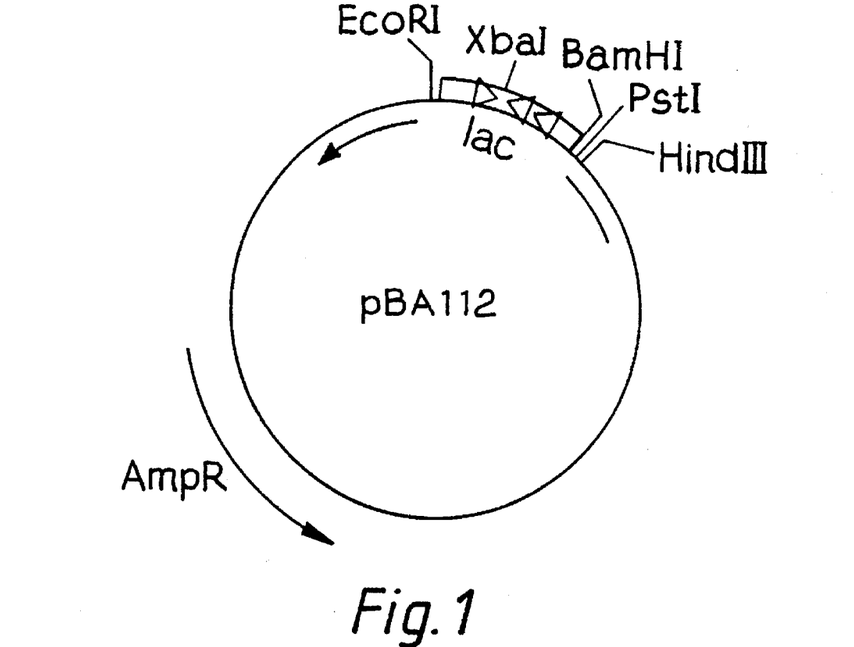
FIG. 1 shows plasmid pBA112 (Andrews, et al., 1985). The thin line represents DNA sequences derived from the bacterial plasmid pUC9; the open bar represents the 74 base-pair DNA fragment containing the FLP recombination site; the triangles indicate the orientation of the three internal DNA repeats within each FLP recombination site (Andrews, et al., 1985)
Figure 2:
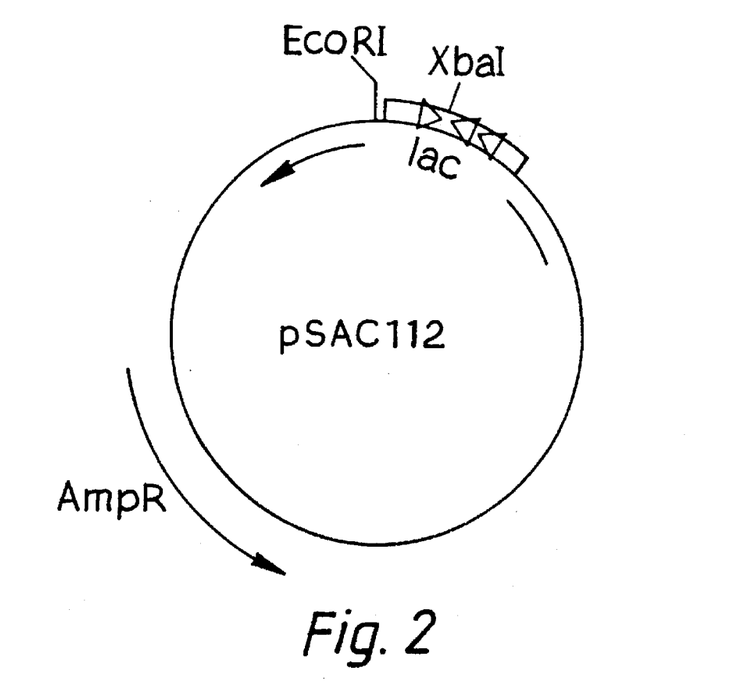
FIG. 2 shows plasmid pSAC112. Plasmid pSAC112 is indentical to pBA112 with the exception that the BamHI, PstI and HindIII sites have been deleted.

Plasmid pSAC112 (FIG. 2) was constructed by digesting plasmid pBA112 (FIG. 1, Andrews, et al., 1985) with the restriction endonucleases BamHI and HindIII simultaneously. Linear plasmid DNA was treated with DNA polymerase I (Klenow) in the presence of 0.3 mM dNTP's (dATP, dTTP, dCTP and dGTP) for 10 minutes at 37° C. DNA was extracted with phenol:chloroform, ethanol-precipitated and incubated overnight at 15° C. in the presence of T4 DNA ligase. Ligated DNA was transformed into E. coli, strain MC1061 (Casadaban and Cohen, 1980); plasmid pSAC112 was isolated from the resultant transformants following identification and characterisation by the method of Birnboim and Doly (1980).

Plasmid pSAC3 (FIG. 3) was constructed by the following procedure. Yeast 2 μm plasmid DNA was isolated from strain DRI9 as described by Guerineau, et al., (1974). Purified 2 μm plasmid DNA was partially digested with the restriction endonuclease XbaI as described by Maniatis et al., (1982), and ligated with XbaI cleaved pSAC112. Ligated DNA was transformed into E. coli, strain AG1 (obtained from NBL Enzymes Ltd., Cramlington, England.). The resultant ampicillin-resistant transformants were screened for homology to 2 μm plasmid DNA following colony hybridization (Grunstein and Hogness, 1975) to $^{32}$P labelled 2.2 kilo base-pair EcoRI fragment from plasmid pYF92 (Storms, R. K. et al., 1979). Colonies showing homology with the 2 μm specific DNA probe were isolated and their plasmid DNA characterized by restriction endonuclease mapping procedures. Plasmid pSAC3 was thus obtained.

Figure 4:
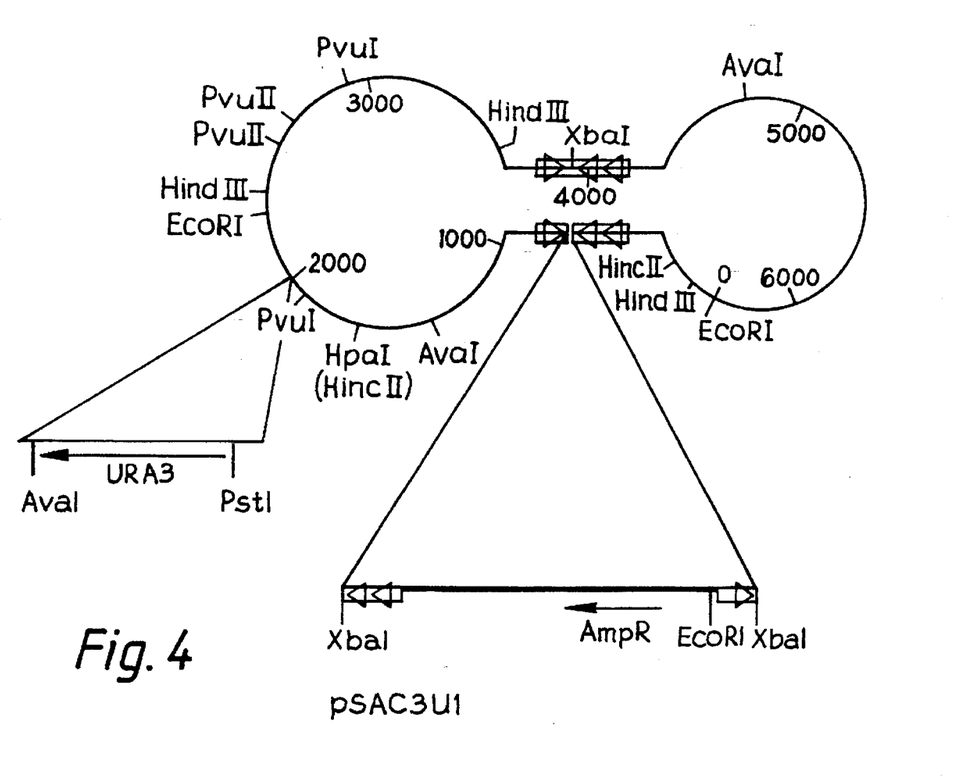
FIG. 4 shows plasmid pSAC3U1. Designations are as for FIG. 3.
Figure 5:
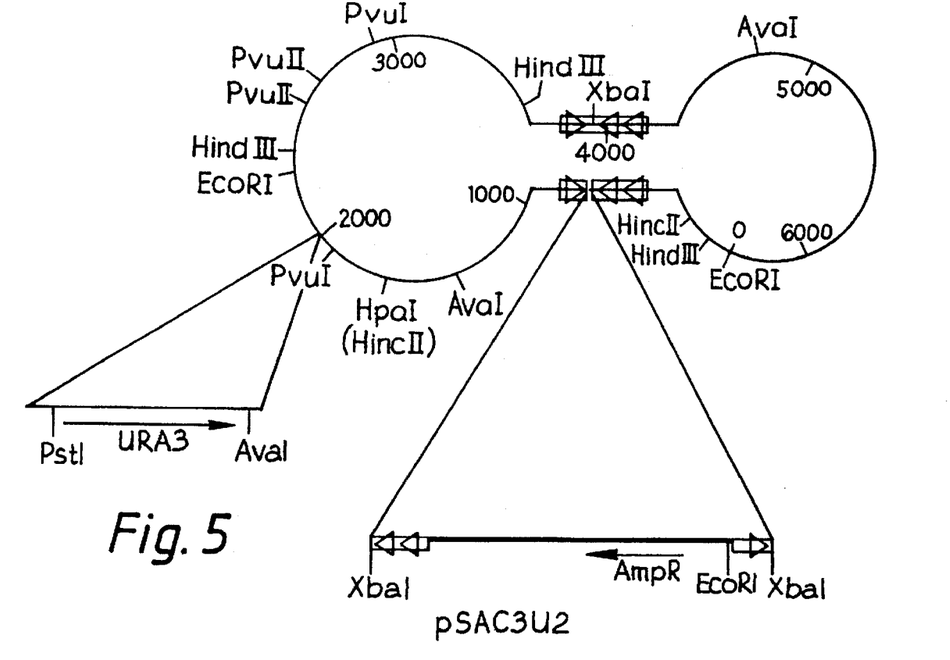
FIG. 5 is a plasmid map of pSAC3U2. Designations are as for FIG. 3.
Figure 6:
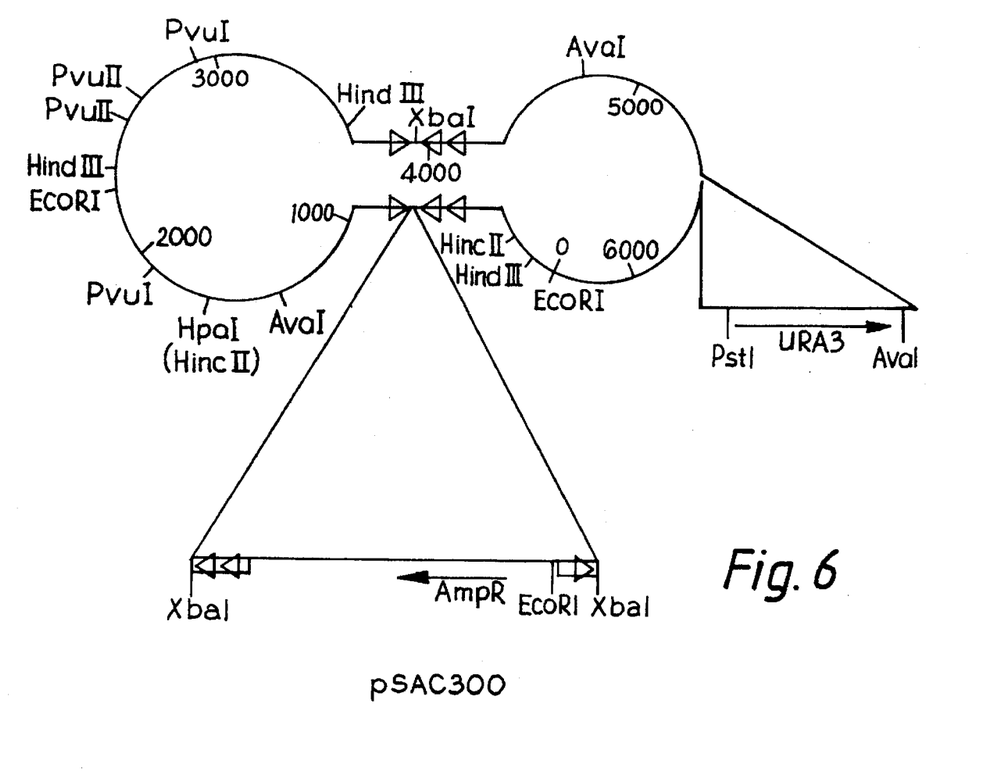
FIG. 6 is a plasmid map of pSAC300. Designations are as for FIG. 3.
Figure 7:
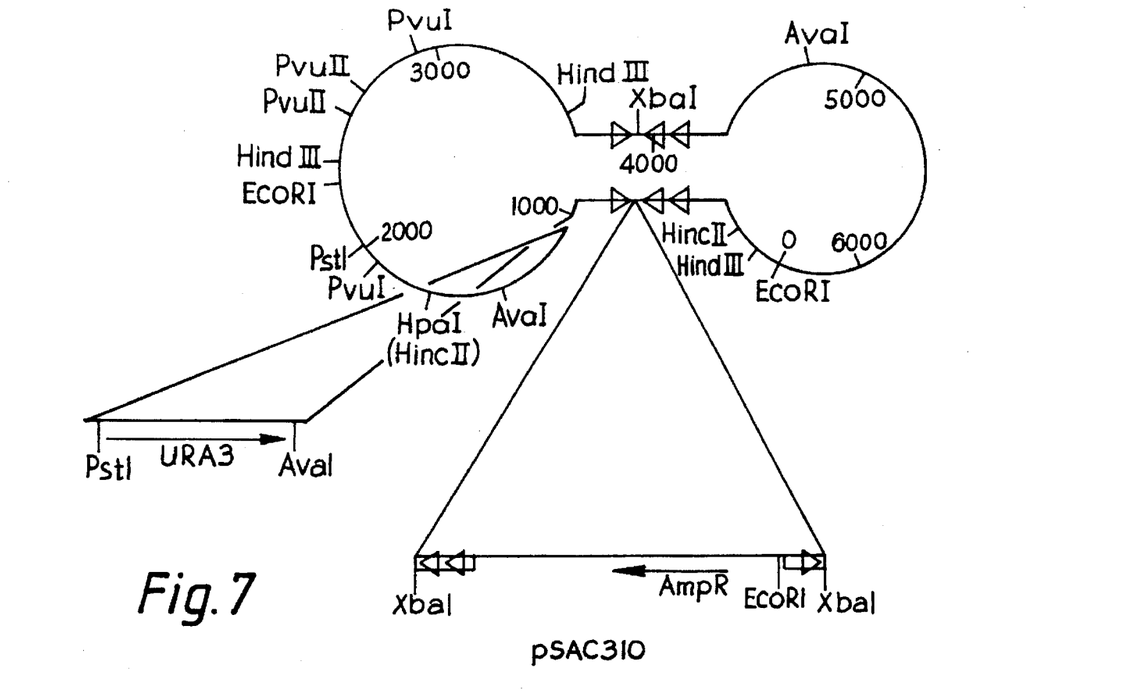
Figure 8:
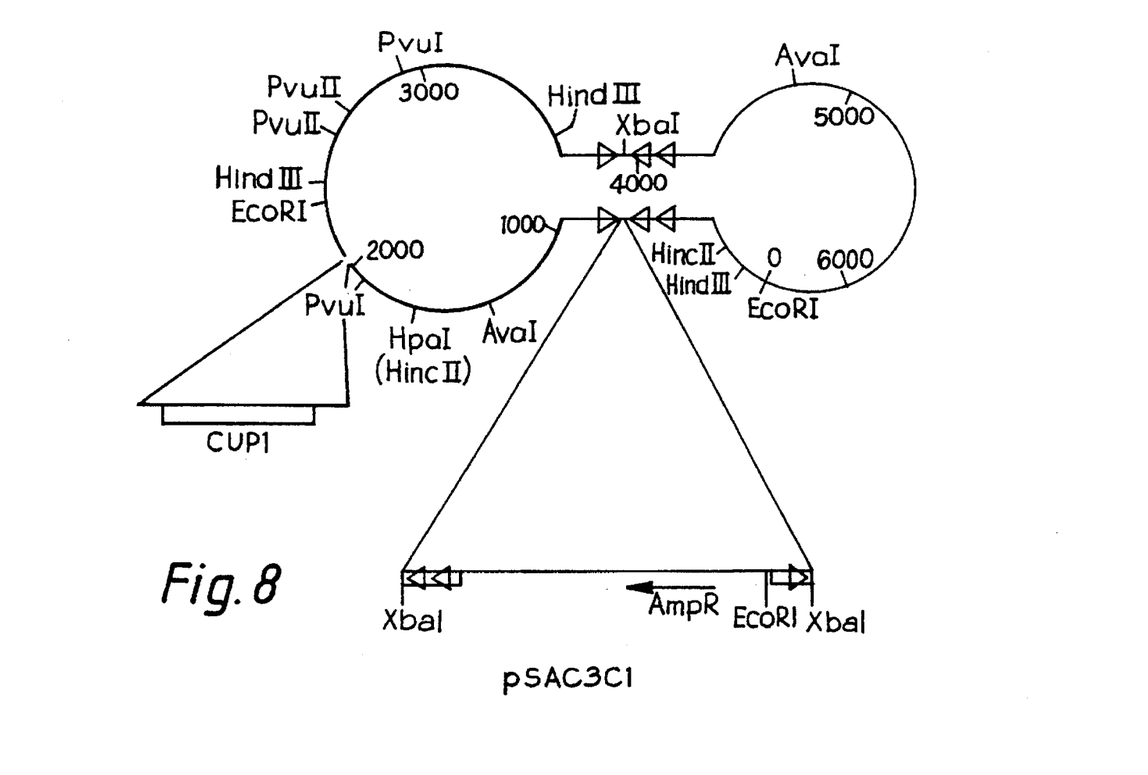
FIG. 8 is a plasmid map of pSAC3C1. Designations are as for FIG. 3.

Plasmids pSAC3U1 (FIG. 4) and pSAC3U2 (FIG. 5) were constructed by cleaving plasmid pSAC3 with the restriction endonuclease PstI. Linear DNA was rendered flush-ended by treatment with T4 DNA polymerase in the presence of 0.3 mM dNTP's (dATP, dTTP, dCTP and dGTP) for 10 minutes at 37° C. DNA was extracted with phenol: chloroform and ethanol-precipitated prior to ligation. Plasmid pJDB110 (Beggs, 1981) was digested with the restriction endonuclease HindIII and the DNA fragments were subjected to agarose gel electrophoresis on a 1% gel. A 1.1 kilo-base-pair DNA fragment, harbouring the URA3 gene of yeast, was isolated from the gel (Maniatis, et al., 1982) and treated with DNA polymerase I (Klenow) in the presence of 0.3 mM dNTP's (dATP, dTTP, dCTP and dGTP). The 1.1 kilo-base-pair HindIII fragment was extracted with phenol:chloroform, ethanol-precipitated and blunt-end ligated with linear pSAC3 DNA prepared as described above. Ligated DNA was transformed into *E. coli*, strain AG1. The resultant ampicillin resistant transformants were screened for homology with the URA3 gene following colony hybridization (Grunstein and Hogness, 1975) to a $^{32}$P labelled 1.1 kilo-base-pair HindIII fragment purified from plasmid pJDB110. Plasmids pSAC3U1 (FIG. 4) and pSAC3U2 (FIG. 5) were isolated from the colonies which showed homology to the URA3 gene probe. The 1.1 kilo-base-pair HindIII DNA fragment carrying the URA3 gene was also blunt-end ligated into the unique EagI and SnaBI sites of pSAC3 to give plasmids designated pSAC300 (FIG. 6) and pSAC310 (FIG. 7) respectively. Plasmid pSAC3C1 (FIG. 8) was constructed by blunt end ligating a 694 base-pair XbaI-KpnI DNA fragment, carrying the CUPI gene from plasmid pET13:1 (Henderson et al., 1985) into the unique PstI site of pSAC3.

Transformation of Yeast with Plasmids pSAC3U1 and pSAC3U2

Figure 9:
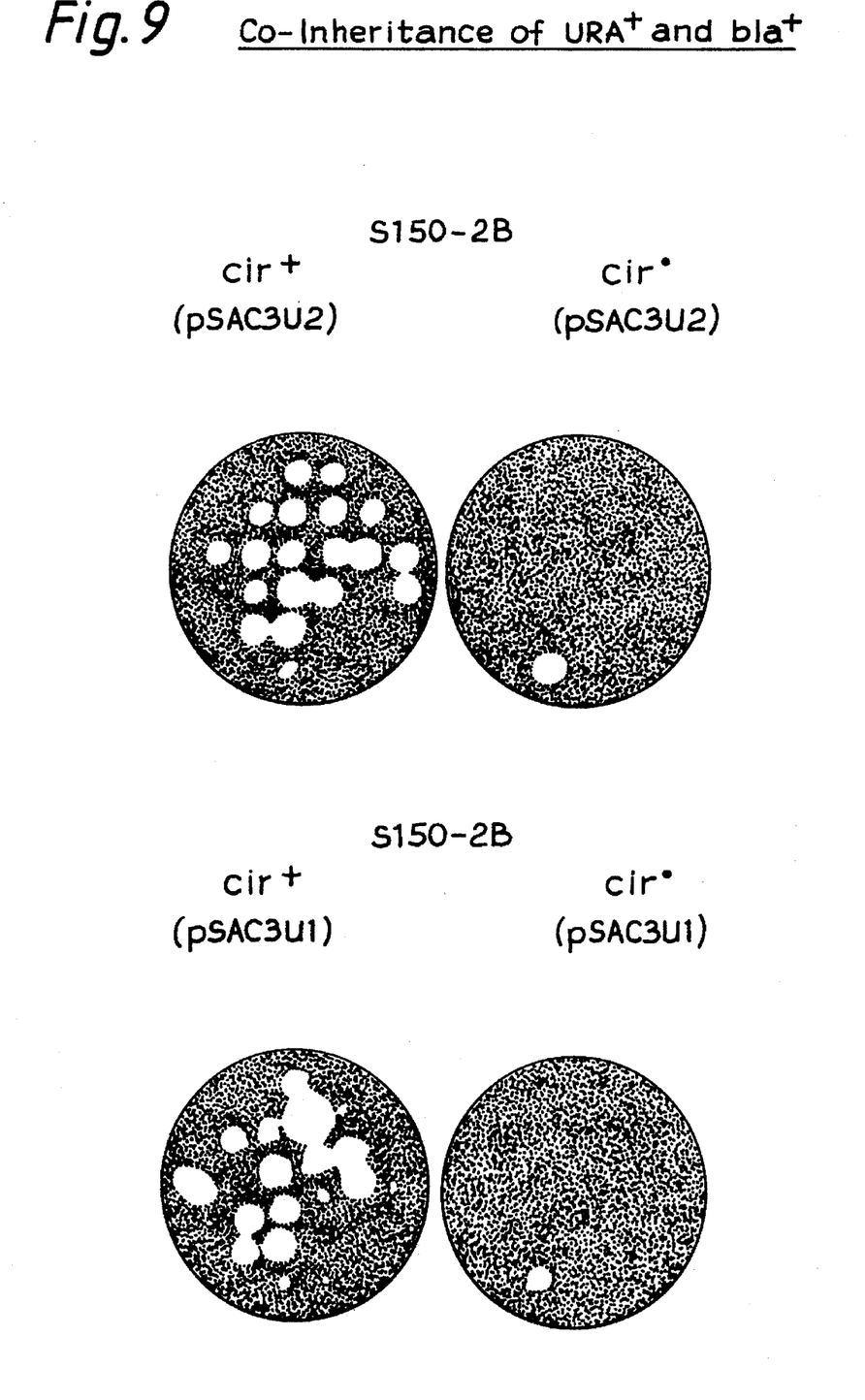
FIG. 9 is based on a photograph showing the growth of haploid yeast strains and illustrates the co-inheritance of the URA3 and bacterial bla gene.

The disintegration vectors pSAC3U1 (FIG. 4) and pSAC3U2 (FIG. 5) were constructed so that they each contain the selectable yeast gene, URA3, inserted at the unique PstI site of 2 µm B form. In addition, each plasmid harbours DNA sequences derived from the bacterial plasmid pUC9 flanked by two copies of the FLP recombination site located in direct orientation. The position of the pUC9 DNA is such that FLP mediated recombination between these two directly orientated FLP recombination sites resulted in the excision of the bacterial plasmid DNA upon transformation of yeast. Cir$^+$ and cir$^0$ derivatives of the haploid yeast strain S150-2B (Cashmore, et al., 1986) were transformed to uracil prototrophy with plasmids pSAC3U1 and pSAC3U2, according to the method of Ito (1983). URA$^+$ transformants were screened for the co-inheritance of the bacterial bla gene, which encodes the β-lactam specific enzyme β-lactamase in yeast, by the method of Chevalier and Aigle (1979). The results presented in FIG. 9 show that both plasmids segregate the bla gene from the URA$^+$ gene in all transformants of the cir$^0$ strain, indicating deletion of the bacterial DNA sequences from the plasmids upon yeast transformation. However, the majority of URA$^+$ transformants of the cir$^+$ strain were observed to co-inherit the bla gene (15 out of 20 and 18 out of 20 for pSACSU1 and pSAC3U2, respectively). These data suggest that the efficiency of plasmid disintegration, i.e. FLP mediated excision of the bacterial plasmid DNA sequences, is greater upon transformation of a cir$^0$ strain than a cir$^+$.

Molecular Analysis of Transformants

In order to determine whether the URA$^+$ transformants which had segregated the bla gene (i.e. β-lactamase negative clones, bla$^-$) had indeed lost the bla gene and adjacent bacterial plasmid DNA sequences, yeast DNA was analysed. Two URA$^+$ bla$^-$ transformants of the cir$^+$ and cir$^0$ strains transformed with pSAC3U1 and pSAC3U2 were grown on selective minimal medium lacking uracil and total DNA was extracted by the following procedure. Actively growing cells were harvested and resuspended in 5 ml 1M sorbitol, 0.025M ethylenediamine-tetracetic acid (EDTA) pH8.0, 8 mg/ml dithiothreitol at 28° C. for 15 minutes. Cells were harvested and resuspended in 5 ml 1.2M sorbitol, 0.1M sodium citrate, 0.01M EDTA pH8, 0.025 µl/ml zymolyase (Kirin Brewery Co. Ltd.) at 28° C. until protoplasts were obtained. Protoplasts were washed three times in 1.2M sorbitol prior to resuspending in 1 ml 3% sarkosyl, 0.M tris/HCl pH7.5, 0.2M EDTA, 100 ul/ml proteinase K at 55° C. for 60 minutes. DNA preparations were extracted with chloroform:iso-propanol, phenol, chloroform and ether prior to dialysis against 10 mM tris/HCl 1 mM EDTA pH8. Total yeast DNA was digested with the restriction endonucleases EcoRI, XbaI and PstI and DNA fragments were separated by agarose electrophoresis. Following Southern transfer (Maniatis, et al., 1982) total yeast DNA was hybridized to $^{32}$P labelled pSAC3 DNA. The results are presented in FIG. 10 which is an autoradiograph of total yeast DNA probed with $^{32}$P labelled pSAC3 DNA. DNA was isolated from S150-2B cir$^+$ strains transformed with plasmids pSAC 3U1 and pSAC 3U2. Two independent transformants of each strain/plasmid combination designated A and B were analysed. DNA was digested with restriction endonuclease as follows: XbaI, tracks 1–4 and 21–24; PstI, tracks 5–12; EcoRI, tracks 3–20.

Figure 10:
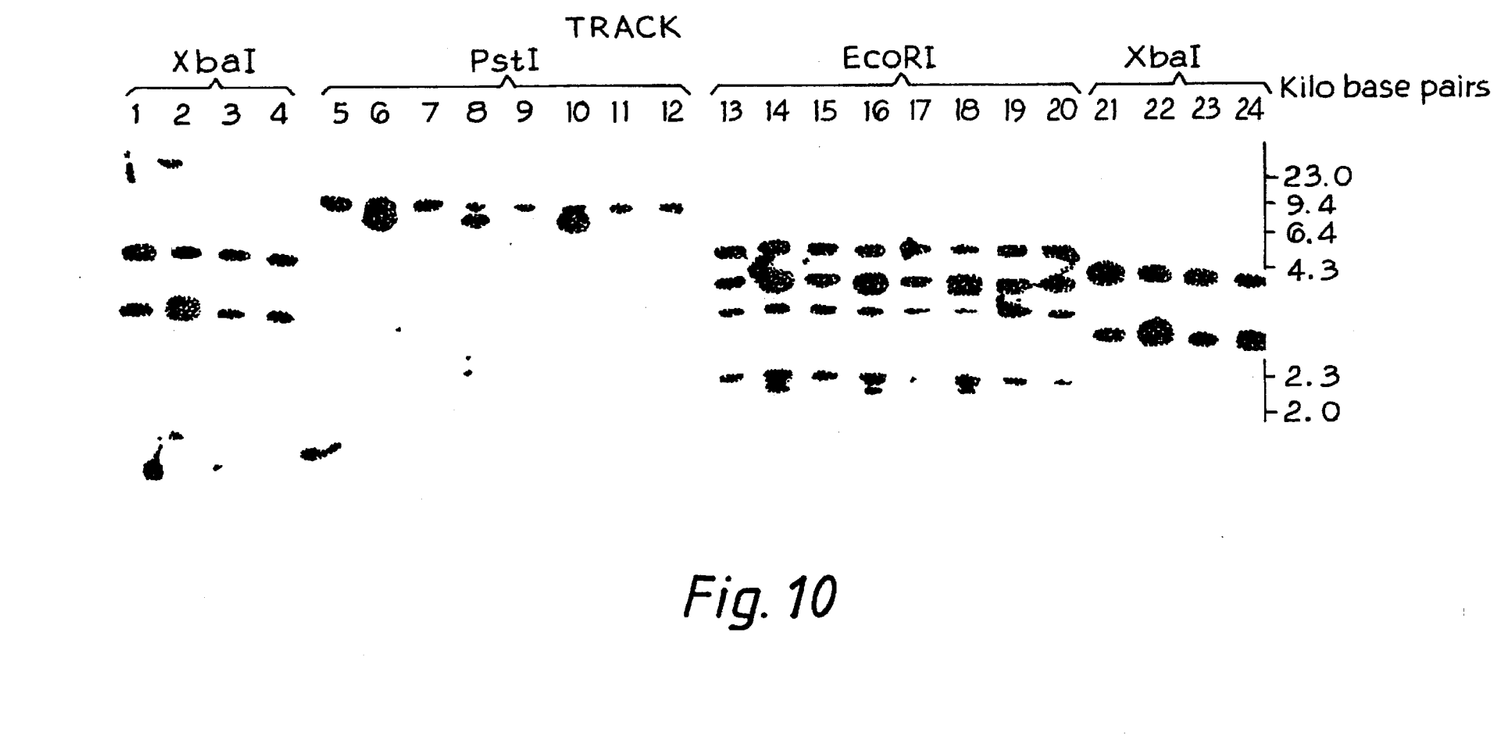
FIG. 10 is an autoradiograph of total yeast DNA probed with $^{32}$P labelled pSAC3 DNA.

| Track | Plasmid | Cir$^+$/cir$^0$ | Isolate (A/B) |
|---|---|---|---|
| 6, 14, 22 | pSAC3U1 | cir$^+$ | A |
| 8, 16, 24 | pSAC3U1 | cir$^+$ | B |
| 5, 13, 21 | pSAC3U1 | cir$^0$ | A |
| 7, 15, 23 | pSAC3U1 | cir$^0$ | B |
| 2, 10, 18 | pSAC3U2 | cir$^+$ | A |
| 4, 12, 20 | pSAC3U2 | cir$^+$ | B |
| 1, 9, 17 | pSAC3U2 | cir$^0$ | A |
| 3, 11, 19 | pSAC3U2 | cir$^0$ | B |

Based upon the known restriction sites present in the endogenous 2 µm plasmid of yeast (Hartley and Donelson, 1980) and recombinant plasmids pSAC3U1 and pSAC3U2, one can predict the hybridization pattern to plasmid pSAC3. The predicted hybridization pattern is presented in Table 1.

TABLE 1

Expected hybridization pattern of S150-2B cir$^+$ and cir$^0$ derivatives, transformed with pSAC3U1 and pSAC3U2 to pSAC3

| Plasmid DNA | Restriction Endonuclease Fragments (kilobase pairs) | | |
|---|---|---|---|
|  | EcoRI | XbaI | PstI |
| 2 um (endogenous) | 4.1 | 3.2 | 6.3 |
|  | 3.9 | 3.1 |  |
|  | 2.4 |  |  |
|  | 2.2 |  |  |
| pSAC3U1 and pSAC3U2 (intact) | 5.3 | 4.3 | 10.2 |
|  | 4.1 | 3.2 |  |
|  | 0.72 | 2.8 |  |
| pSAC3U1 and pSAC3U2 (disintegrated) | (5.0) | 4.3 | 7.4 |
|  | 4.1 | 3.2 |  |
|  | 3.3 |  |  |
|  | (2.4) |  |  |

The numbers in parenthesis will arise if the disintegrated plasmids have undergone FLP mediated interconversion.

If one compares the result of the hybridization (FIG. 10) with those expected (Table 1) it can be seen that in each transformant the recombinant plasmid has undergone a deletion consistent with the excision of the bacterial plasmid DNA sequences, contained within the directly oriented FLP recombination sites. In addition, in the case of the transformants designated pSAC3U2/B the endogenous 2 µm plasmid of strain S150-2B is no longer present. This implies that transformation of a cir$^+$ strain with plasmid pSAC3U2 results in curing of the endogenous 2 µm plasmid.

Additional evidence that plasmids pSAC3U1 and pSAC3U2 undergo an excision of the bacterial plasmid DNA upon transformation of yeast was obtained by hybridizing the aforementioned DNA preparations to $^{32}$P labelled pUC9 DNA (Vieira and Messing, 1982). URA$^+$ bla$^-$ transformants did not hybridize to this DNA probe.

Plasmids pSAC300, pSAC310 and pSAC3C1 Disintegrate upon Yeast Transformation

The URA⁺ plasmids pSAC300 and pSAC310 were used to transform the cir⁺ and cir° derivatives of S150-2B and the URA and bla phenotypes of the resultant transformants were determined. In all cases the disintegrated phenotype was observed; thus pSAC300 and pSAC310 are capable of excising the bacterial vector DNA upon yeast transformation. In this respect it was observed that plasmid pSAC300 gave rise to a significantly higher proportion of bla⁻ transformants of the cir⁺ derivative of S150-2B. The explanation for this is unknown. However it is possible that the disruption of the EagI site by the insertion of the URA3 gene in pSAC300 may have interfered with the expression of the adjacent FLP gene, resulting in over expression of the FLP recombinase.

Plasmid pSAC3C1 was designed to be used in the transformation of copper sensitive industrial yeast and in particular brewing yeast. Thus pSAC3C1 was transformed into a proprietary strain of Bass lager yeast designated BB was described by Hinchliffe and Daubney (1986). Copper resistant transformants were then checked for the presence of the bla phenotype by the β-lactamase plate assay. Approximately 18% of the transformants tested were bla⁻ copper resistant, indicative of the in vivo disintegration of plasmid pSAC3C1 in the brewing yeast host.

The in vivo disintegration of plasmids pSAC300, pSAC310 and pSAC3C1 was subsequently confirmed following a full molecular characterization of the appropriate host strains possessing the disintegrated phenotype. Thus when total yeast DNA was hybridized to $^{32}$P-pUC9 DNA as described previously no homology could be detected in the bla⁻ derivatives.

Plasmid Stability of the 'Disintegrated' Transformants

The inheritable stability of the URA⁺ phenotype in the cir⁺ and cir° strains of S150-2B harbouring the disintegrated derivatives of pSAC3U1 and pSAC3U2, pSAC300 and pSAC310 was determined by growing the yeast non-selectively in YPD containing 2% w/v glucose, plating on the same medium and replica plating to minimal medium lacking uracil. The percent plasmid loss per generation was calculated and is presented in Table 2.

TABLE 2

| | Percent Plasmid Loss per Generation | |
|---|---|---|
| Plasmid Derivative | Percent Plasmid Loss per Generation | |
| (Disintegrated Vector) | S150-2B cir⁺ | S150-2B cir° |
| pSAC3U1 | 0.22 | 0.19 |
| pSAC3U2 | 0.31 | 0.14 |
| pSAC300 | 2.5 | — |
| pSAC310 | 0 | 0.89 |

It can be seen from the result presented in Table 2 that all the 'disintegrated' derivatives are unstable in both the cir⁺ and cir° derivatives of S150-2B. However, the level of instability observed for pSAC3U1, pSAC3U2, and pSAC310 in particular is at least one order of magnitude lower than that observed for other URA⁺2 µm based recombinant vectors in S150-2B (Cashmore, et al., 1986).

It is interested to note that the insertion of the URA3 gene into the unique EagI site of the 2 µm portion of pSAC3 results in a disintegrated derivative which is considerably less stable than those disintegrants derived from pSAC3U1, pSAC3U2 and pSAC310. It is apparent therefore that the site of insertion of the selectable marker can have a profound effect upon the stability of the resultant disintegrated derivative. In this respect it is clear that the unique SnaB1 and PstI sites of 2 µm form suitable loci for the introduction of recombinant genes, since plasmid stability is not adversely affected by such insertions.

Plasmid Stability of 'Disintegrated' Transformants of Brewing Yeast

Disintegrated derivatives of pSAC3C1 transformants of BB11.0 were also analysed for the stability of the copper resistant phenotype. Plasmid stability experiments were performed as described previously and resulted in an estimate of 0.014% plasmid loss per generation, under non-selective growth conditions. It is apparent from this result that the disintegrated derivatives of pSAC3C1 are extremely stable in the brewing yeast strain BB11.0 possessing a degree of stability hitherto unobserved for a recombinant 2 µm based yeast vector.

Disintegration Vectors can be used to Stably Maintain "Genes of Interest" in Yeast Plasmid pSAC3 carries a unique PstI site and a unique SnaBI site into either of which DNA sequences can be inserted as described above, without adversely affecting the phenotype stability of the resultant disintegrated derivative of the plasmid in yeast. These sites can be used as loci for the introduction of "genes of interest" for example the DEX-1 gene of *S.diastaticus* and the human serum albumin gene expressed from a yeast promoter. Using known methods it is possible to insert such genes into these unique loci together with an appropriate selectable marker for yeast transformation. Alternatively, plasmids pSAC3U1, pSAC3U2, pSAC310 and pSAC3C1 can be used as recipients for insertion of an appropriate 'gene of interest'. In this respect pSAC3U1, pSAC3U2 and pSAC310 harbour a unique SmaI site located in the 3' non-translated region of the URA3 gene (Rose et al, 1984). This SmaI site can be used as a locus for the insertion of an appropriate 'gene of interest'.

The desirability of using the SnaBI site to insert a gene of interest, either directly or indirectly (for example when the URA3 gene is inserted and then a gene of interest is inserted into the SmaI site thereof) is independent of the disintegration of the vector, i.e. the loss of the bacterial DNA sequences, and forms another aspect of the invention. Generally speaking, one would wish to prevent transcription continuing from the inserted gene(s) into the endogenous 2 µm regions, particularly into the so-called STB region which is on the side of the SnaBI site remote from the yeast origin of replication (ori). Thus, preferably, the inserted sequence comprises (a) a gene of interest, (b) a promoter therefor on the side thereof adjacent ori and (c) a 3' transcription terminator downstream of the gene of interest and between that gene and the STB region.

REFERENCES

Aigle et al., (1984), *Journal of the American Society of Brewing Chemists*, 42, 1.
Andrews et al., (1985) *Cell*, 40, 795.
Beggs, (1978), *Nature*, 275, 104.
Beggs (1981), In: "Molecular Genetics in Yeast" Alfred Benzon Symposium No: 16, Munksgaard, Copenhagen.
Birnboim & Doly, (1980), *Nucleic Acids Research*, 1513.
Bolivar, (1978), Gene, i, 121.
Botstein & Davis, (1982), In "The Molecular Biology of the Yeast, *Saccharomyces*: Metabolism and Gene Expression", Eds. Strathern et al., Cold Spring Harbour Laboratory, New York.

Broach & Hicks, (1980), *Cell*, 21, 501.
Casadaban & Cohen, (1980), *Journal of Molecular Biology*, 138, 179.
Cashmore, et al., (1986), *Molecular and General Genetics*, 203, 154.
Chevallier & Aigle, (1979), *FEBS Letters*, 108, 179.
Chevallier, et al., (1980), *Gene*, 11, 11.
Clarke & Carbon, (1980), *Nature*, 287, 504.
Clark-Walker & Miklos, (1974), *European Journal of Biochemistry*, 41, 359.
Cohen et al., (1980), *Proceedings of the National Academy of Sciences, USA*, 77, 1078.
Falco & Dumas, (1985), *Genetics*, 109, 21.
Futcher (1986), *Journal of Theoretical Biology*, 119, 197.
Futcher & Cox, (1983), *Journal of Bacteriology*, 154, 612.
Gerbaud et al., (1979), *Gene*, 5, 233.
Gritz et al., (1983), *Gene*, 25, 178.
Grunstein & Hogness, (1975), *Proceedings of the National Academy of Sciences USA*, 72, 3961.
Guerineau, et al., (1974), *Biochemical Biophysics Research Communications*, 61, 462.
Hadfield, et al., (1986), *Gene*, 45, 149.
Hatford & Gathoye, (1985), *DNA*, 80.
Harford & Peters, (1987), *Current Genetics*, 11, 315.
Hartley & Donelson, (1980), *Nature*, 286, 280.
Henderson et al., (1985), *Current Genetics*, 113.
Hicks et al., (1979), Cold Spring Harbour Symposium Quantitative Biology, 4, 1305.
Hinchliffe & Box (1985), *Proceedings of the European Brewery Convention Congress*, 20th, Helsinki, 267.
Hinchliffe & Daubney (1986), *Journal of the American Society of Brewing Chemists*, 98.
Hinnen et al., (1978), *Proceedings of the National Academy of Sciences, USA*, 75, 1929.
Ito et al., (1983), *Journal of Bacteriology*, 153, 163.
Hyman, et al., (1982), *Proceedings of the National Academy of Sciences, USA*, 79, 1578.
Jayaram, et al., (1983), *Cell*, 34, 95.
Jiminez et al., (1980), *Nature*, 28, 869.
Kikuchi, (1983), *Cell*, 35, 487.
Kingsman, et al., (1985) *Biotechnology and Genetic Engineering Reviews*, 377.
Livingston, (1977), *Genetics*, 86, 73.
Livingston & Hahne, (1979), *Proceedings of the National Academy of Sciences., USA*, 76, 3727.
Maniatis et al., (1982), In: "Molecular Cloning: Laboratory Manual", Cold Spring Harbour, N.Y.
Murray et al., (1987), The EMBO Journal 6, 4205
Nelson & Fangman, (1979), *Proceedings of the National Academy of Sciences, USA*, 76, 6515.
Newlon, et al., (1981), ICN-UCLA Symposium on Molecular and Cellular Biology, 22, 501.
Orr-Weaver, et al., (1981), *Proceedings of the National Academy of Sciences, USA*, 78, 6354.
Orr-Weaver, et al., (1983), In "Methods in Enzymology", Eds. Wu, et al., 101, 228, Academic Press, N.Y.
Rine, et al., (1983), *Proceedings of the National Academy of Sciences, USA*, 80, 6750.
Rose et al., (1984), *Gene* 29 133.
Rothstein, (1983), In "Methods in Enzymology", Eds. Wu, et al., 101, 202, Academic Press, N.Y.
Seligy et al., (1980), *Nucleic Acids Research*, 8, 3371.
Sigurdson et al., (1981), *Molecular and General Genetics*, 183, 59.
Som et al., (1988), *Cell* 52, 27
Storms, et al., (1979), *Journal of Bacteriology*, 140, 73.
Struhl et al., (1979), *Proceedings of the National Academy of Sciences, USA*, 76, 1035.
Taketo et al., (1980), *Proceedings of the National Academy of Sciences, USA*, 77, 3144.
Tubb, (1980), *Journal of the Institute of Brewing*, 86, 78.
Vierra & Messing, (1982), *Gene*, 259.
Volkert & Broach, (1986), *Cell*, 46, 541.
Volkert & Broach, (1987), In Press.
Walmsley, et al., (1983), *Molecular and General Genetics*, 192, 361.
Webster & Dickson, (1983), *Gene*, 26, 243.
Winston, et al., (1983), In "Methods in Enzymology", Eds. Wu, et al., 101, 211.
Wu, et al., (1986), In "UCLA Symposium on Molecular and Cellular Biology: Yeast Cell Biology", Ed. Hicks, 323.
Yocum, (1985), European Patent Application No. 163491.

The invention has been described in detail with particular reference to preferred embodiments thereof, but it will be understood that variations and modifications can be effected without departing from the spirit and scope of the invention.

What we claim is:

1. A 2 μm plasmid vector comprising:
   (a) a bacterial DNA sequence,
   (b) yeast 2 μm plasmid-derived DNA comprising three FLP protein binding sites, an origin of replication (ori) and an STB gene, and
   (c) A DNA sequence coding for a protein or peptide of interest, wherein
      one pair of FLP binding sites is in direct orientation and the other two pairs are in indirect orientation,
      the bacterial sequence is located between the FLP binding sites which are in direct orientation such that, when yeast is transformed with the vector, the bacterial sequence is eliminated,
      the DNA sequence which codes for a protein or peptide of interest is not located between the sites which are in direct orientation, and
      the DNA sequence which codes for a protein or peptide of interest is located between ori and the STB gene in the 2 μm plasmid-derived DNA such that transcription of the DNA coding sequence does not continue into ori or STB.

2. A 2 μm plasmid vector according to claim 1 which also comprises a selectable marker DNA sequence.

3. A 2 μm plasmid vector according to claim 1 wherein the bacterial sequence comprises a sequence allowing replication of the vector in a bacterium.

4. A 2 μm plasmid vector according to claim 3 wherein there is no bacterial plasmid DNA sequences which are not between said FLP binding sites in direct orientation.

5. A 2 μm plasmid vector according to claim 1 in which the DNA sequence coding for a protein or peptide of interest is heterologous to yeast.

6. A 2 μm plasmid vector according to claim 5 in which the DNA sequence coding for a protein or peptide of interest is a DNA sequence coding for HSA fused at its 5' terminus to a gene promoter which functions in yeast, via a secretion leader sequence which functions in yeast, and at its 3' terminus to a transcription termination signal which functions in yeast.

7. A 2 μm plasmid vector according to claim 6 in which the DNA sequence coding for a protein or peptide of interest is the MET-HSA gene fused at its 5' terminus to the GAL/CYC1 or GAL/PGK hybrid promoter, and at its 3' terminus to a transcription termination signal which functions in yeast.

8. A 2 μm plasmid vector according to claim 1 in which the DNA sequence coding for a protein or peptide of interest is the *Saccharomyces cerevisiae* var. diastaticus DEX-1 gene or a DNA sequence coding for the β-glucanase of *Bacillus subtilis* fused at its 5' terminus to a gene promoter which functions in yeast, via a secretion leader sequence which functions in yeast, and at its 3' terminus to a transcription termination signal which functions in yeast.

9. A 2 μm plasmid vector according to claim 1 further comprising gene of interest inserted at the SnaBI site.

10. A process for preparing a 2 μm plasmid vector according to any one of the preceding claims comprising:

inserting the DNA sequences which encodes a protein or peptide of interest into a 2 μm plasmid containing (i) an origin of replication (ori) and an STB gene, (ii) a DNA sequence for selecting yeast tranformants, and (iii) an insert comprising (a) bacterial plasmid DNA to allow propagation of the vector in bacteria and (b) the elements of an FLP protein binding site such that an extra FLP protein binding site is created in the vector and the bacterial DNA is located between two FLP protein binding sites that are in direct orientation, said DNA sequence being inserted between ori and the STB gene of the 2 μm plasmid DNA, such that transcription of the DNA sequence does not continue through ori or STB.

11. A process according to claim 10 wherein the insert is inserted at a unique XbaI site in an endogenous 2 μm FLP protein binding site, one end of the insert containing one portion of a 2 μm FLP protein binding site repeat sequence and the other end of the insert containing the remainder of the said repeat sequence.

12. A yeast cell containing a 2 μm plasmid comprising an origin of replication (ori), an STB gene and a DNA sequence encoding a protein or peptide of interest which is heterologous to yeast, the plasmid comprising no bacterial DNA, wherein said DNA sequence which encodes the protein or peptide of interest is located between ori and the STB gene, such that transcription of the DNA sequence does not continue through ori or STB.

13. A 2 μm-based plasmid vector comprising an origin of replication (ori) and an STB gene, a sequence coding for a heterologous protein or peptide inserted between ori and the STB gene and only two FLP protein binding sites, the two binding sites being in direct orientation with bacterial DNA between them such that, upon transforming a yeast cell with the vector, recombination occurs, the bacterial DNA is lost and the resulting plasmid is maintained.

14. Brewing yeast or laboratory yeast transformed with a 2 μm plasmid vector as claimed in any of claims 1 to 9 or 13.

15. A method of using a yeast according to claim 12 in a fermentation to produce a protein or peptide of interest.

16. A method of using a yeast according to claim 14 in a fermentation to produce a protein or peptide of interest.

17. A 2 μm plasmid vector carrying a gene of interest inserted at the SnaB1 site located between ori and the STB gene.

* * * * *